United States Patent [19]

Sipos et al.

[11] 4,235,993
[45] Nov. 25, 1980

[54] N-BENZYLIDENEAMPHOTERICIN B, ITS METHYL ESTER AND PROCESS FOR MAKING WATER-SOLUBLE SALTS THEREOF

[75] Inventors: Frank Sipos, Cranbury; Adam J. Keseleski, Edison, both of N.J.

[73] Assignee: E. R. Squibb & Sons, Inc., Princeton, N.J.

[21] Appl. No.: 13,710

[22] Filed: Feb. 21, 1979

[51] Int. Cl.³ ............................................. C07H 17/08
[52] U.S. Cl. .................................. 536/17 R; 424/180; 536/18
[58] Field of Search .......................... 536/17, 18, 17 R

[56] References Cited

U.S. PATENT DOCUMENTS

| | | | |
|---|---|---|---|
| 4,007,166 | 2/1977 | Kulbakh et al. | 536/17 |
| 4,035,567 | 7/1977 | Sipos | 536/17 |
| 4,035,568 | 7/1977 | Schaffner et al. | 536/17 |
| 4,041,232 | 8/1977 | Sipos et al. | 536/17 |
| 4,144,328 | 3/1979 | Vainshtein et al. | 424/180 |

OTHER PUBLICATIONS

Pigman, "The Carbohydrates," 1957, Academic Press, Inc., New York, N.Y., pp. 406–409.

*Primary Examiner*—Johnnie R. Brown
*Attorney, Agent, or Firm*—Lawrence S. Levinson; Burton Rodney

[57] ABSTRACT

New intermediates, namely, N-benzylideneamphotericin B, and its methyl ester, are employed in a new process for preparing water-soluble salts of amphotericin B, methyl ester, such as amphotericin B, methyl ester aspartate.

16 Claims, No Drawings

N-BENZYLIDENEAMPHOTERICIN B, ITS METHYL ESTER AND PROCESS FOR MAKING WATER-SOLUBLE SALTS THEREOF

FIELD OF THE INVENTION

The present invention relates to new intermediates, namely, N-benzylideneamphotericin B and its methyl ester, to a method for preparing same, and to use of the methyl ester in a method for preparing water-soluble salts of amphotericin B, methyl ester.

BACKGROUND OF THE INVENTION

The methyl ester of amphotericin B which has the formula

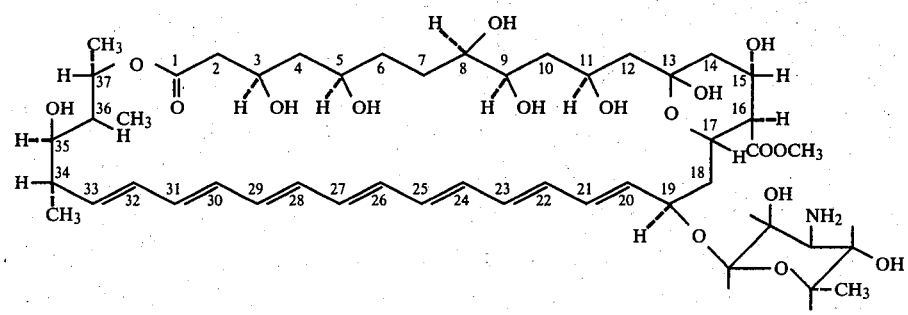

has been prepared by mixing amphotericin B starting material with dimethylsulfoxide and methanol to form a solution of the amphotericin B. The dissolved amphotericin B is then esterified by reaction with diazomethane and the resulting reaction mixture treated with ethyl ether to precipitate the methyl ester.

Belgian Pat. No. 802,512 discloses another procedure for preparing the methyl ester of amphotericin B wherein amphotericin B starting material is mixed with dimethylsulfoxide to form a solution and aqueous ammonia is added to adjust the pH to about 10 (measured on wet indicator paper or after dilution of a sample with water). The solution of amphotericin B is then treated with diazomethane as described above to form the methyl ester.

U.S. Pat. No. 4,035,567 discloses yet another technique for preparing the methyl ester of amphotericin B wherein amphotericin B starting material is mixed with dimethylformamide or hexamethylphosphoric triamide, for a predetermined period; thereafter the above is mixed with sufficient aqueous ammonia to obtain a solution of the amphotericin B, such solution having a pH above 9 in the case where dimethylformamide is used and a pH above 10 in the case where hexamethylphosphoric triamide is used.

After the dissolution of the amphotericin B is effected, esterification is carried out employing diazomethane in accordance with conventional techniques.

While the methyl ester of amphotericin B is particularly valuable for its antifungal properties and in the apparent inability of fungus organisms to develop strains or forms that are resistant to amphotericin B methyl ester, its use has been limited by lack of adequate water solubility.

U.S. Pat. No. 4,041,232 discloses more soluble forms of the methyl ester of amphotericin B which are salts thereof formed by reaction with monocarboxylic amino acids, dicarboxylic amino acids, hydroxy acids, hydrocarbon monocarboxylic acids and hydrocarbon polycarboxylic acids.

DESCRIPTION OF THE INVENTION

A new and improved process is provided for preparing water-soluble salts of the methyl ester of amphotericin B wherein substantially improved purity of such salts are obtained than possible where prior art methods have been employed.

As will be seen hereinafter, the process of the invention includes several steps during which new intermediates, namely, N-benzylideneamphotericin B and the methyl ester of N-benzylideneamphotericin B are formed. Furthermore, the formation of undesirable N-methylated by-products (formed in prior art processes) is substantially reduced.

In one aspect of the present invention, a process is provided for preparing the methyl ester of N-benzylideneamphotericin B which process includes the steps of reacting a dispersion of amphotericin B with benzaldehyde to form N-benzylideneamphotericin B,

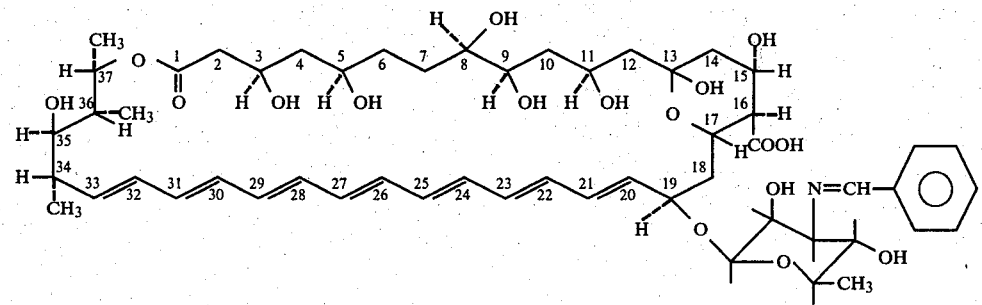

N-Benzylideneamphotericin B and without necessarily isolating the N-benzylideneamphotericin B, reacting same with diazomethane to form the methyl ester of N-benzylidenamphotericin B.

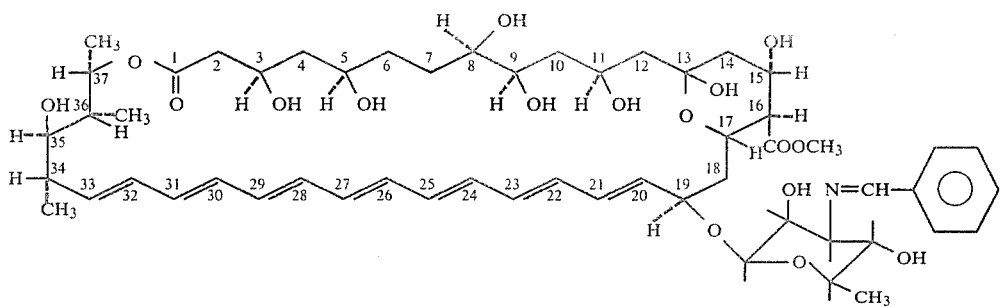

N-Benzylideneamphotericin B, Methyl Ester

In another aspect of the invention, a process is provided for preparing water-soluble salts of the methyl ester of amphotericin B, which process includes the step of reacting the methyl ester of N-benzylideneamphotericin B with an acid or acid derivative to form the corresponding water-soluble salt of the methyl ester of amphotericin B.

In carrying out the reaction of amphotericin B with the benzaldehyde and methanol, the amphotericin B is dispersed, and preferably dissolved, in a solvent therefor, such as an aprotic solvent to provide from about 8 to about 12% solution of amphotericin B. Examples of aprotic solvents which may be employed include dimethylformamide, dimethylsulfoxide, hexamethylphosphoric amide and mixtures thereof, with a mixture of dimethylformamide and dimethylsulfoxide being preferred.

The amphotericin B is reacted with an amount of benzaldehyde to provide a weight ratio of amphotericin B to benzaldehyde of within the range of from about 8:1 to about 4:1, and preferably from about 7:1 to about 6:1, for a period ranging from about 5 to about 20 minutes, prior to adding methanol to the reaction mixture.

The methanol is added in an amount to protect the free hydroxyl groups of the amphotericin B during its reaction with diazomethane. The methanol is added in an amount to provide a weight ratio of amphotericin B to methanol of within the range of from about 1:1 to about 4:1, and preferably from about 2:1 to about 3:1.

After addition of methanol is complete, the reaction mixture is preferably cooled to a temperature of from about $+10°$ C. to about $-10°$ C., and preferably from about $+8°$ C. to about $+2°$ C.

Esterification of the N-benzylidene amphotericin B may be carried out employing diazomethane in accordance with conventional techniques. For example, the reaction mixture containing the N-benzylideneamphotericin B may be cooled below room temperature, for example, within the range of from about $0°$ C. to about $15°$ C., and an excess of diazomethane (the excess ranging from about 100 to about 150% over stoichiometric requirements) in a solvent such as tetrahydrofuran or ethyl ether, is added.

In a preferred embodiment, the diazomethane is generated and co-distilled with a solvent such as tetrahydrofuran and the distillate is added continuously to the reaction mixture containing the N-benzylideneamphotericin B.

The diazomethane may be generated from N-methyl-N-nitroso-p-toluenesulfonamide (Diazald, Aldrich), or other precursors for diazomethane such as N-nitroso-N-methyl urea or N-nitroso-N-methyl urethane, and boiling alcoholic potassium hydroxide. Continual consumption of the diazomethane as it is generated eliminates the danger from the building of large quantities and high concentrations of the diazomethane.

Sufficient diazomethane will be provided to attain a weight ratio of N-benzylideneamphotericin B to diazomethane of within the range of from about 14:1 to about 8:1, and preferably from about 12:1 to about 10:1.

After completion of the reaction with diazomethane (which may be carried out over periods ranging from about 20 to about 60 min., the temperature of the reaction mixture is allowed to rise slightly, and if necessary, the reaction mixture is filtered, for example, with Hyflo. The solvents are then distilled off in vacuo and the residue precipitated, for example, with ethyl acetate. The product, N-benzylideneamphotericin B methyl ester, may then be separated by centrifugation or filtration and dried. To remove the remaining solvent, the dried product may then be triturated with intense agitation in water or in a mixture of acetone-water, filtered and rinsed.

The wet cake (N-benzylideneamphotericin B methyl ester) is thereafter suspended in aqueous medium containing an appropriate acid or acid derivative (1.0 to 2.0 equivalents of the acid) to form the corresponding water-soluble salt of amphotericin B methyl ester which may be separated from the reaction mixture and purified employing conventional technques.

Examples of acids which may be employed in forming the water-soluble salts include monocarboxylic amino acids, dicarboxylic amino acids, hydroxy acids, hydrocarbon monocarboxylic acids and hydrocarbon polycarboxylic acids.

The mono and dicarboxylic amino acids (natural or synthetic) which are suitable for use herein include alanine, asparagine, aspartic acid, cysteine, glutamic acid, glutamine, histidine, isoleucine, leucine, lysine, phenylalanine, sarcosine, serine, threonine, tyrosine and valine and all optical isomers and derivatives thereof, with glutamic acid, aspartic acid and pyroglutamic acid being preferred.

The hydroxy acids suitable for use herein may contain one or two hydroxy groups and up to 12 carbons, and include, but are not limited to, glycolic acid, lactic acid, hydroxybutyric acid and malic acid, including isomers thereof, with lactic acid being preferred.

The hydrocarbon mono and dicarboxylic acid may contain one, two or three carboxyl groups and (up to 15 carbons and) include alkanoic acids, alkenoic acids or aromatic acids. Such acids suitable for use herein include, but are not limited to, formic acid, acetic acid, butyric acid, valeric acid, caproic acid, caprylic acid, capric acid, octanoic acid, glutaric acid, adipic acid, malonic acid, succinic acid, oxalic acid, crotonic acid, oleic acid, acrylic acid, vinylacetic acid, maleic acid, fumaric acid, hydrocinnamic acid, cinnamic acid, mellitic acid, o- or p-toluic acid, phthalic acid, terephthalic acid or naphthoic acid, with acetic acid being preferred.

Examples of acid derivatives which may be employed herein include acetyl glycine and t-butyloxycarbonyl-proline.

Preferred salts of the amphotericin B methyl ester include aspartic acid salt, the glutamic acid salt, pyroglutamic acid salt and the acetic acid salt.

In general, aqueous solutions containing from 0.1 to 10% by weight of the salts will have a pH within the range of from about 4.5 to about 6.5, and preferably from about 5.8 to about 6.2.

The salts of the invention are readily water soluble, that is, have a solubility of 10% or more, and are as stable as and may be more stable than, and as active as the methyl ester of amphotericin B.

Where the acid or acid derivative is a mono carboxylic acid, it is preferred that 1:1 molar ratios of the acid and ester be employed. However, where dicarboxylic acids are employed, it is preferred that a weight ratio of acid:ester of within the range of from about 1:1 to about 1:2 and more preferably 1:2 be employed.

The salts of the invention retain the anti-fungal activity of amphotericin B methyl ester, are stable in the dry form as well as in solution, and are readily soluble in water so as to permit the preparation of concentrated aqueous solutions in the range of from about 2 g to 120 g per liter. Such concentrated aqueous solutions may be used, for example, to control fungal growths in the digestive tract of fowl by supplying it to the drinking water.

The following Examples represent preferred embodiments of the present invention.

EXAMPLE 1

N-Benzylideneamphotericin B

In a 5 liter flask, 200 g of amphotericin B are dissolved in 800 ml of dimethylformamide and 800 ml of dimethylsulfoxide. 25 ml of Benzaldehyde are added and the reaction mixture is stirred for 5 minutes. Thereafter, 100 ml of methanol are added. The reaction mixture is cooled in an ice-water bath maintaining the temperature at 5°±3° C. throughout the reaction.

The reaction mixture is found to contain N-benzylideneamphotericin B.

EXAMPLE 2

N-Benzylideneamphotericin B Methyl Ester 200 g N-Methyl-N-nitroso-p-toluenesulfonamide (Diazald, Aldrich) are dissolved in 1400 ml of tetrahydrofuran.

A solution of alcoholic KOH is next prepared by dissolving 70 g of KOH in 100 ml water and diluting with 300 ml of ethanol. The alcoholic KOH solution is placed in a 2 liter flask, a few boiling chips are added, and the solution is heated to close to boiling point (~75° C.)

The N-methyl-N-nitroso-p-toluenesulfonamide (Diazald) solution is added dropwise from a dropping funnel to the gently boiling solution of alcoholic KOH to generate diazomethane. The diazomethane in tetrahydrofuran is distilled into the cold solution of N-benzylideneamphotericin B (prepared in Example 1).

The reaction mixture is concentrated on a rotary evaporator to 500±50 ml and with vigorous agitation the concentrated dark reddish-brown solution is slowly poured in 15 liters of cold ethyl acetate. The resulting bright yellow suspension is filtered, the cake washed with ethyl acetate, and the product dried in vacuo to yield 200±15 g of N-benzylideneamphotericin B methyl ester.

EXAMPLE 3

Amphotericin B Methyl Ester-L-Aspartate

The crude N-benzylideneamphotericin B methyl ester (200±15 g) from Example 2 is suspended and agitated in 1200 ml of water. The suspension is filtered for 2 to 10 hours, and the cake washed with water or acetone-water mixture.

The wet cake of N-benzylideneamphotericin B methyl ester is suspended in 2800 ml water containing 12 g of L-aspartic acid. The suspension is stirred for 20–60 minutes to achieve dissolution. The solution is extracted with 600 ml of methylisobutylketone, the separated water phase is filtered with 100 g of Hyflo through a Hyflo cake on a Buchner funnel. The filtrate is evaporated on a rotary evaporator to ⅔ of its original volume. The residue is diluted with water to a 5–7% solution, filtered and then lyophilized.

The lyophilized product is triturated with 3 liters of dry acetone, filtered and dried in vacuo over $P_2O_5$ for at least 24 hours.

The yield of amphotericin B methyl ester aspartate (2:1) is 150–180 g (69–83%).

EXAMPLE 4

Amphotericin B methyl Ester Glutamate (Salt)

Following the procedure of Example 3, N-benzylidene amphotericin B methyl ester (200 g) is added in portions to a suspension of L-glutamic acid (1:1 molar ratio) in water and the mixture is stirred until complete dissolution. The clear solution is thereafter freeze dried. The yield is quantitative. The product has a solubility in water of about 10% or more at RT.

EXAMPLE 5

Amphotericin B Methyl Ester-Pyroglutamate

Following the procedure of Example 3, N-benzylidene amphotericin B methyl ester (200 g) is added in portions to a solution of pyroglutamic acid (1:1 molar ratio) in water and stirred until dissolution (5–10 minutes). The clear solution is thereafter lyophilized. The resulting product is found to be very soluble in water (more than 10% soluble at RT).

EXAMPLE 6

Amphotericin B Methyl Ester Acetate

Following the procedure of Example 3, N-benzylidene amphotericin B methyl ester (200 g) is added in portions to a solution of acetic acid (1:1 molar ratio) in water and stirred until complete dissolution. The clear solution is then lyophilized. The product when dissolved in water (1%) has a pH of 5.8 to 6.4 and a solubility greater than 10% at RT.

EXAMPLE 7

Amphotericin B Methyl Ester Propionate

Following the procedure of Example 3, N-benzylidene amphotericin B methyl ester is added in portions to a solution of propionic acid in 1:1 molar ratio in water and stirred until dissolution. The clear solution is then lyophilized.

EXAMPLE 8

Amphotericin B Methyl Ester Octanoate

Following the procedure of Example 3, N-benzylidene amphotericin B methyl ester is added in portions to a solution of octanoic acid in 1:1 molar ratio in water and stirred until dissolution. The clear solution is then lyophilized.

EXAMPLE 9

Amphotericin B Methyl Ester Laurate

Following the procedure of Example 3, N-benzylidene amphotericin B methyl ester is added in portions to a solution of lauric acid in 1:1 molar ratio in water and stirred until dissolution. The clear solution is then lyophilized.

EXAMPLE 10

Amphotericin B Methyl Ester Formate

Following the procedure of Example 3, N-benzylidene amphotericin B methyl ester is added in portions to a solution of formic acid in 1:1 molar ratio in water and stirred until dissolution. The clear solution is then lyophilized.

EXAMPLE 11

Amphotericin B Methyl Ester Lactate

Following the procedure of Example 3, N-benzylidene amphotericin B methyl ester is added in portions to a solution of lactic acid in 1:1 molar ratio in water and stirred until dissolution. The clear solution is then lyophilized.

EXAMPLE 12

Amphotericin B Methyl Ester Alaninate

Following the procedure of Example 3, N-benzylidene amphotericin B methyl ester is added in portions to a solution of alanine in 1:1 molar ratio in water and stirred until dissolution. The clear solution is then lyophilized.

EXAMPLE 13

Amphotericin B Methyl Ester Carbamate

Following the procedure of Example 3, N-benzylidene amphotericin B methyl ester is added in portions to a solution of carbamic acid in 1:1 molar ratio in water and stirred until dissolution. The clear solution is then lyophilized.

EXAMPLE 14

Amphotericin B Methyl Ester Sarcosinate

Following the procedure of Example 3, N-benzylidene amphotericin B methyl ester is added in portions to a solution of sarcosine in 1:1 molar ratio in water and stirred until dissolution. The clear solution is then lyophilized.

EXAMPLE 15

Amphotericin B Methyl Ester Valinate

Following the procedure of Example 3, N-benzylidene amphotericin B methyl ester is added in portions to a solution of valine in 1:1 molar ratio in water and stirred until dissolution. The clear solution is then lyophilized.

EXAMPLE 16

Amphotericin B Methyl Ester Leucinate

Following the procedure of Example 3, N-benzylidene amphotericin B methyl ester is added in portions to a solution of leucine in 1:1 molar ratio in water and stirred until dissolution. The clear solution is then lyophilized.

EXAMPLE 17

Amphotericin B Methyl Ester Isovalinate

Following the procedure of Example 3, N-benzylidene amphotericin B methyl ester is added in portions to a solution of isovaline in 1:1 molar ratio in water and stirred until dissolution. The clear solution is then lyophilized.

EXAMPLE 18

Amphotericin B Methyl Ester Phenylalaninate

Following the procedure of Example 3, N-benzylidene amphotericin B methyl ester is added in portions to a solution of phenylalanine in 1:1 molar ratio in water and stirred until dissolution. The clear solution is then lyophilized.

EXAMPLE 19

Amphotericin B Methyl Ester Serinate

Following the procedure of Example 3, N-benzylidene amphotericin B methyl ester is added in portions to a solution of serine in 1:1 molar ratio in water and stirred until dissolution. The clear solution is then lyophilized.

EXAMPLE 20

Amphotericin B Methyl Ester Cysteinate

Following the procedure of Example 3, N-benzylidene amphotericin B methyl ester is added in portions to a solution of cysteine in 1:1 molar ratio in water and stirred under dissolution. The clear solution is then lyophilized.

EXAMPLE 21

Amphotericin B Methyl Ester Ornithinate

Following the procedure of Example 3, N-benzylidene amphotericin B methyl ester is added in portions to a solution of ornithine in 1:1 molar ratio in water and stirred until dissolution. The clear solution is then lyophilized.

EXAMPLE 22

Amphotericin B Methyl Ester Histidinate

Following the procedure of Example 3, N-benzylidene amphotericin B methyl ester is added in portions to a solution of histidine in 1:1 molar ratio in water and stirred until dissolution. The clear solution is then lyophilized.

EXAMPLE 23

Amphotericin B Methyl Ester Hydroxyprolinate

Following the procedure of Example 3, N-benzylidene amphotericin B methyl ester is added in portions to a solution of hydroxyproline in 1:1 molar ratio in water and stirred until dissolution. The clear solution is then lyophilized.

EXAMPLE 24

Amphotericin B Methyl Ester Threoninate

Following the procedure of Example 3, N-benzylidene amphotericin B methyl ester is added in portions to a solution of threonine in 1:1 molar ratio in water and stirred until dissolution. The clear solution is then lyophilized.

EXAMPLE 25

Amphotericin B Methyl Ester Isoleucinate

Following the procedure of Example 3, N-benzylidene amphotericin B methyl ester is added in portions to a solution of isoleucine in 1:1 molar ratio in water and stirred until dissolution. The clear solution is then lyophilized.

EXAMPLE 26

Amphotericin B Methyl Ester Norleucinate

Following the procedure of Example 3, N-benzylidene amphotericin B methyl ester is added in portions to a solution of norleucine in 1:1 molar ratio in water and stirred until dissolution. The clear solution is then lyophilized.

EXAMPLE 27

Amphotericin B Methyl Ester Norvalinate

Following the procedure of Example 3, N-benzylidene amphotericin B methyl ester is added in portions to a solution of norvaline in 1:1 molar ratio of water and stirred until dissolution. The clear solution is then lyophilized.

EXAMPLE 28

Amphotericin B Methyl Ester Acrylate

Following the procedure of Example 3, N-benzylidene amphotericin B methyl ester is added in portions to a solution of acrylic acid in 1:1 molar ratio in water and stirred until dissolution. The clear solution is then lyophilized.

EXAMPLE 29

Amphotericin B Methyl Ester Valerate

Following the procedure of Example 3, N-benzylidene amphotericin B methyl ester is added in portions to a solution of valeric acid in 1:1 molar ratio in water and stirred until dissolution. The clear solution is then lyophilized.

EXAMPLE 30

Amphotericin B Methyl Ester Glutarate

Following the procedure of Example 3, N-benzylidene amphotericin B methyl ester is added in portions to a solution of glutaric acid in 2:1 molar ratio in water and stirred until dissolution. The clear solution is then lyophilized.

EXAMPLE 31

Amphotericin B Methyl Ester Adipate

Following the procedure of Example 3, N-benzylidene amphotericin B methyl ester is added in portions to a solution of adipic acid in 2:1 molar ratio in water and stirred until dissolution. The clear solution is then lyophilized.

EXAMPLE 32

Amphotericin B Methyl Ester Malonate

Following the procedure of Example 3, N-benzylidene amphotericin B methyl ester is added in portions to a solution of malonic acids in 2:1 molar ratio in water and stirred until dissolution. The clear solution is then lyophilized.

EXAMPLE 33

Amphotericin B Methyl Ester Succinate

Following the procedure of Example 3, N-benzylidene amphotericin B methyl ester is added in portions to a solution of succinic acid in 2:1 molar ratio in water and stirred until dissolution. The clear solution is then lyophilized.

What is claimed is:

1. A compound selected from the group consisting of N-benzylideneamphotericin B and the methyl ester of N-benzylideneamphotericin B.

2. A process for preparing water-soluble salts of the methyl ester of amphotericin B, which comprises reacting amphotericin B with benzaldehyde to form N-benzylideneamphotericin B, reacting the N-benzylideneamphotericin B with diazomethane to form N-benzylideneamphotericin B, methyl ester, reacting the N-benzylideneamphotericin B, methyl ester with an acid selected from the group consisting of monocarboxylic amino acids, dicarboxylic amino acids, hydroxy acids, hydrocarbon carboxylic acids and hydrocarbon polycarboxylic acids, to cleave the benzylidene group off and form the corresponding water-soluble salt of the methyl ester of amphotericin B.

3. The process as defined in claim 2 wherein the compound N-benzylideneamphotericin B, methyl ester is prepared by admixing a dispersion of amphotericin B with benzaldehyde and methanol, and admixing the so-formed mixture with diazomethane to form N-benzylideneamphotericin B, methyl ester.

4. The process defined in claim 3 wherein the amphotericin B is dispersed in an aprotic solvent selected from the group consisting of dimethylformamide, dimethylsulfoxide, hexamethylphosphoramide, and mixtures thereof.

5. The process as defined in claim 3 wherein the amphotericin B is employed in a weight ratio to the benzaldehyde of within the range of from about 8:1 to about 4:1.

6. The process as defined in claim 4 wherein the amphotericin B is dissolved in a mixture of dimethylformamide and dimethylsulfoxide.

7. The process as defined in claim 6 wherein the dimethylformamide is employed in a weight ratio to the dimethylsulfoxide of within the range of from about 1:1 to about 10:1.

8. The process as defined in claim 3 wherein the diazomethane is dissolved in tetrahydrofuran.

9. The process as defined in claim 3 wherein the diazomethane is generated from N-methyl-N-nitroso-p-toluenesulfonamide (Diazald) and boiling alcoholic alkali metal hydroxide, and a solution of diazomethane in tetrahydrofuran is distilled into the mixture.

10. The process as defined in claim 3 wherein after methanol and benzaldehyde are added, the reaction mixture is cooled to between $+10°$ C. and $-10°$ C.

11. The process as defined in claim 2 wherein said acid is a monocarboxylic amino acid employed in a molar ratio to the N-benzylideneamphotericin B, methyl ester of within the range of from about 1:1 to about 2:1.

12. The process as defined in claim 2 wherein said acid is a dicarboxylic amino acid employed in a molar ratio to the N-benzylideneamphotericin B, methyl ester of within the range of from about 1:2 to about 1:1.

13. The process as defined in claim 2 wherein said reaction is carried out in an aqueous medium or an aqueous-acetone medium.

14. The process as defined in claim 2 wherein said amino acid is aspartic acid, glutamic acid, pyroglutamic acid, glycine, glycin, alanine, valine, leucine, isovaline, phenylalanine, tyrosine, sarcosine, serine, cysteine, methionine, norvaline, norleucine, isoleucine, threonine, thyroxine, arginine, lysine, ornithine, asparagine, citrulline, histidine, tryptophan, pyroline or hydroxyproline.

15. The process as defined in claim 14 wherein said amino acid is aspartic acid.

16. The process as defined in claim 15 wherein said aspartic acid is employed in a weight ratio to the N-benzylideneamphotericin B, methyl ester of within the range of from about 1:12 to about 1:8.

* * * * *